United States Patent [19]
Ohmura et al.

[11] Patent Number: 5,773,233
[45] Date of Patent: Jun. 30, 1998

[54] MONOCLONAL ANTIBODY SPECIFIC TO NITRIFYING BACTERIA AND METHOD FOR DETECTION THEREOF

[75] Inventors: Hiroshi Ohmura; Takekazu Okumura; Fumiko Nagai, all of Tokyo, Japan

[73] Assignee: Kabushiki Kaisha Yakult Honsha, Tokyo, Japan

[21] Appl. No.: 738,654

[22] Filed: Oct. 30, 1996

[30] Foreign Application Priority Data

Nov. 2, 1995 [JP] Japan .................................. 7-309890
Jun. 28, 1996 [JP] Japan .................................. 8-188444

[51] Int. Cl.$^6$ ........................ G01N 33/53; G01N 33/554; C07K 16/00; C12P 21/08
[52] U.S. Cl. .......................... 435/7.32; 435/7.1; 435/326; 435/332; 435/340; 530/388.2; 530/388.4
[58] Field of Search .................... 435/7.1, 7.32, 435/340, 326, 332; 530/388.2, 388.4

[56] References Cited

FOREIGN PATENT DOCUMENTS

WO95/25958  9/1995  WIPO .

OTHER PUBLICATIONS

Sevier et al (Clinical Chemistry vol. 27 No. 11 pp. 1797–1806), 1981.

*Primary Examiner*—Anthony C. Caputa
*Assistant Examiner*—Mark Navarro
*Attorney, Agent, or Firm*—Oblon, Spivak, McClelland, Maier & Neustadt, P.C.

[57] ABSTRACT

The present invention relates to a monoclonal antibody showing a high specificity to *Nitrosomonas europaea* or *Nitrobacter agilis*, and a monoclonal antibody-sensitized latex for detecting *Nitrosomonas europaea* or *Nitrobacter agilis* used for facilitating the detection of nitrifying bacteria present in activated sludge, water, soil or microorganism-immobilized carriers, and besides a method of detecting nitrifying bacteria using said monoclonal antibody-sensitized latex. The present invention provides a monoclonal antibody to nitrifying bacteria having ammonia oxidation activities or nitrite oxidation activities present in activated sludge or soil, or microorganism-immobilized carriers. This monoclonal antibody to *Nitrosomonas europaea* or *Nitrobacter agilis* is prepared by culturing clones of fused cells (hybridomas) obtained by fusing antibody-forming cells and tumor cells obtained from an animal immunized with *Nitrosomonas europaea* or *Nitrobacter agilis*.

7 Claims, 2 Drawing Sheets

MONOCLONAL ANTIBODY SPECIFIC TO NITRIFYING BACTERIA AND METHOD FOR DETECTION THEREOF

TECHNICAL FIELD

The present invention relates to a monoclonal antibody showing a high specificity to *Nitrosomonas europaea* (ammonia oxidation bacteria) or *Nitrobacter agilis* (nitrate oxidation bacteria), and a monoclonal antibody-sensitized latex for detecting *Nitrosomonas europaea* or *Nitrobacter agilis* used for facilitating the detection of nitrifying bacteria present in activated sludge, water, soil or microorganism-immobilized carriers, and besides a method of detecting nitrifying bacteria using said monoclonal antibody-sensitized latex. More specifically, the present invention provides a monoclonal antibody to nitrifying bacteria having ammonia oxidation activities or nitrite oxidation activities present in activated sludge or soil, or microorganism-immobilized carriers. This is a monoclonal antibody to *Nitrosomonas europaea* or *Nitrobacter agilis* prepared by culturing clones of fused cells (so-called hybridomas) obtained by fusing antibody-forming cells and tumor cells obtained from an animal immunized with *Nitrosomonas europaea* or *Nitrobacter agilis*. The present invention provides a novel monoclonal antibody capable of detecting active target microorganisms present in activated sludge or soil, or microorganism-immobilized carriers and serving to establish a method for the precise quantitative analysis of the number of bacteria, and a monoclonal antibody-sensitized latex for detecting *Nitrosomonas europaea* or *Nitrobacter agilis* using said antibody, and besides a method for the detection and the quantitative analysis thereof.

BACKGROUND OF ARTS

As a method of facilitating the detection of nitrifying bacteria present in activated sludge or soil has generally been known a method comprising picking up samples, culturing them for one to two months, and then measuring them indirectly according to the formation and the consumption of nitrite in said samples (see "Method of Tests on Soil Microorganisms" by Ryusuke Kimura et al., pp. 207–214 (1992)). In addition, it has been performed by utilizing such a method of measurement to control the movement of active target microorganisms present in activated sludge or soil. According to said method, however, the detection and measurement of target microorganisms have required technical expertise or have taken a long period of time, and hence it has been hard to take a rapid correspondence to control the movement of target microorganisms from the results of measurement.

On the other hand, the present inventors have developed a method of detecting ammonia oxidation bacteria or nitrite oxidation bacteria using an antibody, and have proposed a method of detecting ammonia oxidation bacteria or nitrite oxidation bacteria rapidly according to said method (official gazette of Japanese Laid-Open Patent Publication No. 5-322896. In addition, the present inventors have proposed a method of detecting ammonia oxidation bacteria, nitrite oxidation bacteria and besides denitrifying bacteria more easily using an antibody-sensitized latex comprising said antibody adsorbed on latex particles (Japanese Laid-Open Patent Application No. 8-29426). However, since said antibody is a polyclonal antibody, an antibody being formed differs according to an animal used individually, and it has been hard to obtain always uniform products in specificity, binding capacity and antibody titer. And therefore, it has been hard to standardize the properties of an antiserum reagent, and there has been a possibility of variability of the results of an inspection by the reagent. In addition to a problem upon individual variations of animals, there may occur a problem in the stage of the formation of an antibody; moreover, there have been various problems including the co-existence of antibody molecules with various properties formed by antibody-forming cells of numerous different clones possessed by immunized animals.

Under these circumstances, the present inventors have engaged in assiduous studies with a view to preparing a monoclonal antibody making it possible to obtain antibodies always significantly uniform in specificity and binding capacity according to antigen information, applying the technique of the tissue culture of cells without depending on only immunized animals, and establishing a new method of detecting nitrifying bacteria using said monoclonal antibody, and as a result have succeeded in preparing an anti-*Nitrosomonas europaea* monoclonal antibody and an anti-*Nitrobacter agilis* monoclonal antibody specifically recognizing Gram-negative chemoautotroph bacteria *Nitrosomonas europaea* having ammonia-removing activities and Gram-negative chemoautotroph bacteria *Nitrobacter agilis* having nitrite-removing activities, and at the same time in establishing a new method for the detection of the same using said monoclonal antibody, which has led to the accomplishment of the present invention.

That is, it is an object of the present invention to provide a novel monoclonal antibody to *Nitrosomonas europaea* and *Nitrobacter agilis* of nitrifying bacteria, and in addition, it is another object of the present invention to provide a method of producing the monoclonal antibody and a method of detecting *Nitrosomonas europaea* and *Nitrobacter agilis* using a monoclonal antibody-sensitized latex and analyzing quantitatively the number of bacteria at a high sensitivity.

SUMMARY OF THE INVENTION

The present invention provides a novel monoclonal antibody capable of detecting active target microorganisms present in activated sludge or soil, or microorganism-immobilized carriers and serving to establish a method for the precise quantitative analysis of the number of bacteria, and a monoclonal antibody-sensitized latex for detecting *Nitrosomonas europaea* or *Nitrobacter agilis* using said antibody, and besides a method for the detection and the quantitative analysis thereof. The monoclonal antibody to *Nitrosomonas europaea* or *Nitrobacter agilis* is prepared by culturing clones of fused cells (hybridomas) obtained by fusing antibody-forming cells and tumor cells obtained from an animal immunized with *Nitrosomonas europaea* or *Nitrobacter agilis*.

DISCLOSURE OF THE INVENTION

Figure 1:
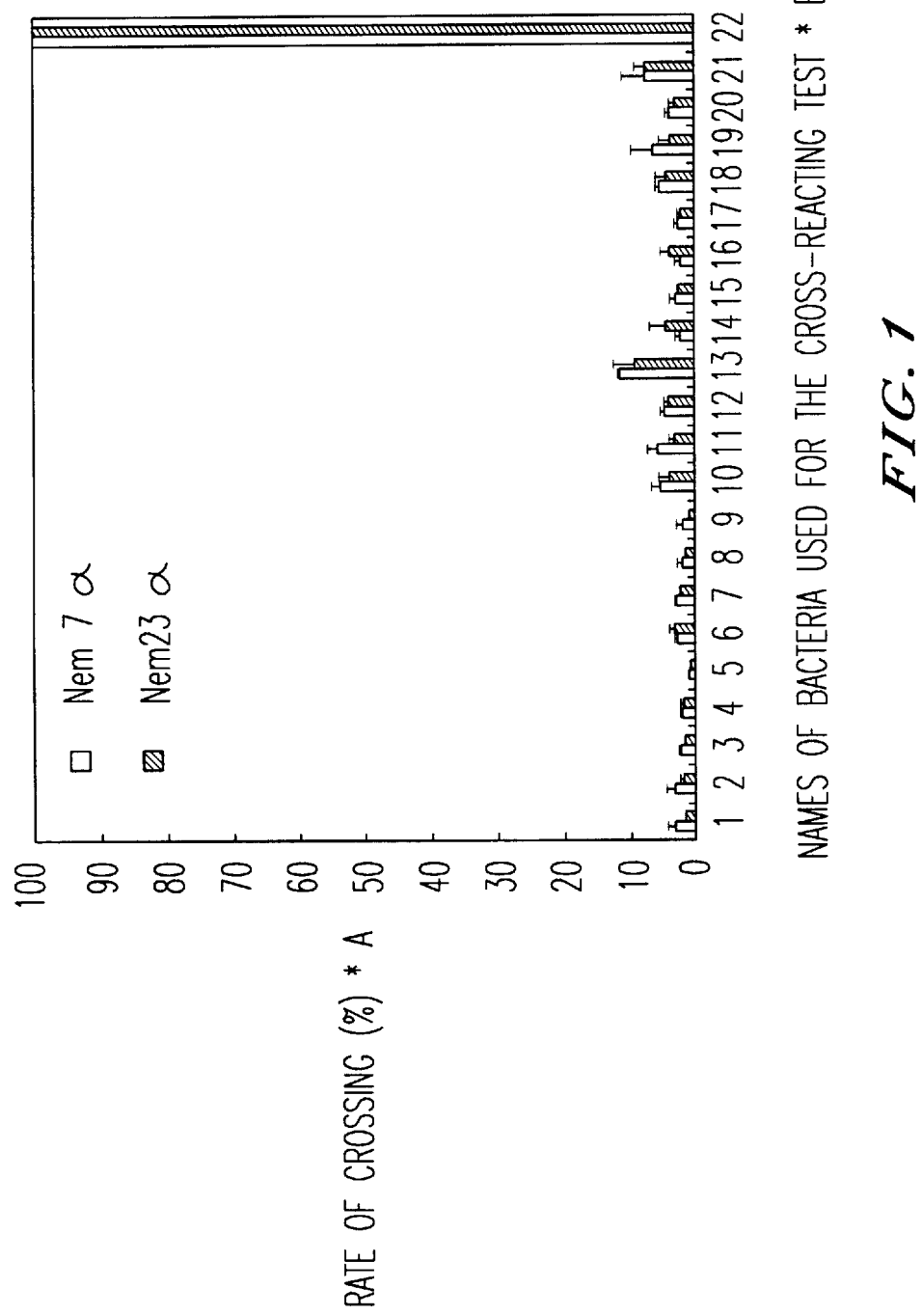
FIG. 1 shows the results of investigation the specificity of a purified monoclonal antibody.

The present invention for dissolving the above problems relates to an anti-*Nitrosomonas europaea* monoclonal antibody recognizing *Nitrosomonas europaea* specifically, and an anti-*Nitrobacter agilis* monoclonal antibody recognizing *Nitrobacter agilis* specifically, and the above anti-*Nitrosomonas europaea* monoclonal antibody and the above anti-*Nitrobacter agilis* monoclonal antibody recognizing the antigen-determining sites of the above two kinds of bacterial cells specifically are preferable modes of embodiment.

Moreover, the present invention relates to fused cells (hybridomas) forming the above anti-*Nitrosomonas europaea* monoclonal antibody and the above anti-*Nitrobacter agilis* monoclonal antibody, and an antibody-sensitized latex for *Nitrosomonas europaea* and *Nitrobacter agilis* characterized by compressing a monoclonal antibody specific for *Nitrosomonas europea* and *Nitrobacter agilis* adsorbed on latex particles, and the above antibody-sensitized latex of *Nitrosomonas europaea* and *Nitrobacter agilis* with latex particles having a high specific gravity of around 1.5 g/cc, and the above antibody-sensitized latex of *Nitrosomonas europaea* and *Nitrobacter agilis* with latex particles having an average particle diameter of around 1.0 μm are preferable modes of embodiment.

Furthermore, the present invention relates to a method for the detection and the quantitative analysis of *Nitrosomonas europaea* and *Nitrobacter agilis* characterized by using the above antibody-sensitized latex for *Nitrosomonas europaea* and *Nitrobacter agilis*.

Hereunder, the present invention will be described more specifically with *Nitrobacter agilis* as an example.

The same mode of embodiment is employed for *Nitrosomonas europaea*, which is omitted here.

A novel monoclonal antibody according to the present invention is produced as follows. That is, the anti-*Nitrobacter agilis* monoclonal antibody is produced by immunizing an animal with Gram-negative chemoautotroph bacteria *Nitrobacter agilis* having nitrite-removing activities, forming fused cells (hybridomas) between antibody-forming cells obtained from the animal and tumor cells, subsequently proliferating said fused cells, selecting cells forming an antibody showing specificity to *Nitrobacter agilis* from the proliferated fused cells, and culturing the antibody-forming cells produce the same. An anti-*Nitrobacter agilis* monoclonal antibody according to the present invention is extremely useful as a reagent for the quantitative analysis of the number of bacteria of *Nitrobacter agilis* present in activated sludge or soil, or as a reagent to be used for maintaining and controlling nitrifying bacteria having ammonia/nitrite oxidation activities in microorganism-immobilized carriers.

The above fused cells (so-called hybridomas) are formed by fusing cells forming an antibody to *Nitrobacter agilis* obtained from an animal immunized with said *Nitrobacter agilis* (hereinafter referred to as *Nitrobacter agilis* antibody-forming cells) and myeloma cells of tumor cells. *Nitrobacter agilis* antibody-forming cells to be used are preferably spleen cells from an animal immunized with *Nitrobacter agilis*. In connection with the above *Nitrobacter agilis* antibody-forming cells and myeloma cells, it is not necessary to specify the kinds of animals as a supply source so far as fusing is possible; from the viewpoints of fusing efficiency and the stability of the formation of an antibody, however, those derived from the same kind of animals are employed preferably.

As to the above hybridomas, those obtained by fusing spleen cells of a mouse immunized with *Nitrobacter agilis* and myeloma cells of the mouse are preferable, and examples thereof include hybridomas obtained by fusing anti-*Nitrobacter agilis* antibody-forming spleen cells of a BALB/c mouse immunized with *Nitrobacter agilis* in advance and spleen cells of the BALB/c mouse.

After fusing the cells, a clone forming an antibody showing specificity to cells of *Nitrobacter agilis* or antigen-determining sites thereof is selected by cloning the hybridomas, culturing the thus obtained clones, and selecting the clone from numerous clones obtained.

For the detection of an antibody, an enzyme immunoassay (ELISA method) reported by Voller et al. (Bull. WHO., Vol. 53, pp. 55–56, (1976)) is employed preferably.

The above point will be described more specifically hereunder; a hybridoma culture broth or ascites of a mouse inoculated with hybridomas is added to a *Nitrobacter agilis* antigen immobilized on the the wells of a tissue culture plate, for example, a 99-well microtiter plate, and subsequently an anti-mouse immunoglobulin antibody labeling peroxidase is added therein, and then the peroxidase activities of it are examined according to the color development of orthophenylene diamine (OPD). The color development of OPD means the presence of an antibody. The titer of the anti-*Nitrobacter agilis* monoclonal antibody to the hybridoma culture broth, the concentrated solution thereof, or ascites inoculated with hybridomas are shown by the final dilution rate of a specimen showing the color development of OPD (measured value at an absorbance of 492 nm) of 0.5 or 1.0. Serum and ascites obtained by inoculating a culture broth of myeloma cells P3-NS1-1-Ag4-1 (hereinafter referred to as NS-1) of a BALB/c mouse and said cells on a BALB/c mouse have no antibody activity to *Nitrobacter agilis*.

The production of a monoclonal antibody to *Nitrobacter agilis* is performed by maintaining and growing the above antibody-forming clones in a medium, or in the body of a histocompatibility animal or a nude mouse. Or it is recovered from the serum or ascites of an animal (regarding a method of recovery, see Monoclonal Antibody by Tatsuo Iwasaki et al., pp. 88–94, (1983)).

Besides, latex particles of carriers adsorbing the above specific monoclonal antibody, and a method of producing a sensitized latex can be performed according to the method reported by the present inventors.

That is, regarding the latex particles, latex particles having a specific gravity of as high as 1.0 to 1.5 g/cc, preferably around 1.5 g/cc are employed preferably, and latex particles having an average particle diameter of about 0.8 to 2.2 μm, preferably around 1.0 μm are employed preferably.

As such latex particles can be exemplified commercially available products such as Bactlatex 0.81 (manufactured by Difco, average particle diameter: 0.81 μm, specific gravity: 1.0 g/cc), and H0901, H0902 and H2002 (manufactured by Nihon Gosei Gomu, average particle diameter/specific gravity: 0.94 μm·1.5 g/cc, 0.98 μm·1.5 g/cc and 2.22μm·1.5 g/cc, respectively); however, they are not restricted to the above, and those having the same effect can be used irrespective of kind thereof.

An antibody-sensitized latex can also be obtained by mixing a suspension of latex particles diluted with a proper buffer solution and a buffered solution of an antibody; in this case, as said buffered solution can be employed an ammonium chloride-buffered saline solution, a PBS buffer solution and a glycine-buffered saline solution, and the glycine-buffered saline solution is preferred from the viewpoints of causing preferable agglutination of an antibody-sensitized latex and hardly causing self-agglutination of it.

The concentration of an antibody-sensitized latex is preferably from 0.05 to 1.0%, more preferably from 0.1 to 0.5%, most preferably around 0.25%.

The concentration of an antibody protein at sensitization is preferably from 0.05 to 0.3%; otherwise it becomes hard to distinguish between positive and negative reaction of it due to the decrease of sensitivity and the self-agglutination of an antibody-sensitized latex.

Moreover, a sensitized-latex reaction is performed at a temperature within the range of 0° to 60° C.; if the reaction is performed at room temperature or at a temperature a little higher than room temperature (to 40° C.), a latex with an excellent sensitivity can be obtained.

In order to perform the detection of nitrifying bacteria and the measurement of the number of bacteria using these sensitized latices, a sample solution diluted to a proper grade is mixed with a sensitized-latex solution to confirm the dilution rate capable of observing agglutinated images, while a mixing test using a standard sample of a bacterial solution is performed, and the number of bacteria is calculated according to a comparison with the results thereof.

As a specific method thereof, a mictotiter method capable of judging with the naked eye simply can be employed. That is, the method is comprising sampling an antigen diluted with a buffer solution stepwise or a sample solution on a U-shaped mictotiter plate, introducing an antibody-sensitized latex into each well and leaving it to stand at room temperature for 3 to 15 hours, and then observing and judging it with the naked eye or using an about 10× magnifier.

Specifically, in this case, agglutinated images of each well are judged by deeming agglutinated images in the case of using only a buffer solution as negative, and the number of bacteria is calculated from the dilution rate of the tested well showing positive agglutinated images and the results of an agglutination test employing a standard antigen.

In the present invention, it goes without saying that various methods of detection and quantitative analysis using a monoclonal antibody-sensitized latex adsorbing a monoclonal antibody of nitrifying bacteria, such as a method comprising mixing a monoclonal antibody-sensitized latex according to the present invention and a sample to be tested on a slide glass and judging agglutinated images light-microscopically (microscope latex method), can be utilized.

BEST MODE FOR CARRYING OUT THE INVENTION

Hereunder, the present invention will be described in more detail with reference to Examples but is not deemed to be limited thereto.

EXAMPLE 1

Preparation of an anti-*Nitrosomonas europaea* Monoclonal Antibody
(1) Preparation of Hybridomas and Production of an Ascites Antibody Pure-cultured *Nitrosomonas europaea* was washed with a physiological saline solution, and then suspended in a physiological saline solution to adjust the value at an absorbance of 660 nm to 0.5. The obtained suspension (0.2 ml) was injected into a tail vein of a BALB/c mouse, and 10 days after, 0.2 ml of a suspension prepared in the same manner were injected therein to additionally. In addition, the suspension was injected therein to 4 or 5 times in total every 10 days. Before the mouse was slaughtered, 0.2 ml of a suspension prepared in the same manner were injected therein to as the final immunity. The mouse was killed on the 4th day after the final immunity to extract the spleen, and the spleen cells were suspended in the RPMI1640 medium (produced by Sigma). A suspension solution of the spleen cells was treated with a 0.82% aqueous ammonium, chloride solution at room temperature for 10 minutes, then washed in a serum-free medium twice according to centrifugal separation (250×g), and subsequently suspended in a serum-free medium.

Separately, NS-1 cells were proliferated in the RPMI1640 medium containing 15% of fetal bovine serum, then washed in a serum-free medium twice according to centrifugal separation, and subsequently suspended in a serum-free medium. After $4.0 \times 10^7$ spleen cells and $1.0 \times 10^7$ NS-1 cells in a suspended state were mixed, the mixture were subjected to centrifugal separation to precipitate the cells; 1 ml of a serum-free medium containing 45% of polyethylene glycol 6000 was added therein, and the cells were fused at 37° C. for 6 minutes. The obtained cell mixture was washed in a serum-free medium according to centrifugal separation, and then suspended in the RPMI1640 medium containing 15% of fetal bovine serum to adjust to be $1.0 \times 10^5$ spleen cells/ml, and 0.1 ml thereof was introduced into a 96-well plastic microtiter plate, and cultured in an incubator in the presence of 7% hydrocarbon gas.

On the first day after the start of the culture, 0.1 ml of the HAT medium was added therein, and thereafter half of the culture broth was sucked to remove on the second day, on the 4th day, on the 7th day and on the 10th day, and instead of them the HAT medium was added respectively. Colonies of hybridomas, 1 to 2 per well on an average, were grown in 60 to 90% of culture wells of the 96-well plastic microtiter plate. When the hybridomas were proliferated fully (about two weeks after the start of the culture), the antibody titer of the culture supernatant liquid to *Nitrosomonas europaea* was examined according to an enzyme immunoassay. Antibodies to *Nitrosomonas europaea* were recognized in the culture supernatant liquid of 154 wells of the total wells. A cloning operation according to limiting dilution was performed twice repeatedly about hybridomas of each well forming antibodies. Thus, two clones forming antibodies stably were separated. These clones were named Nem 7 α and Nem 23 α respectively. The clone Nem 7 α was deposited at National Institute of Bioscience and Human-Technology Agency of Industrial Science and Technology under the deposit No. of FERM BP-5675, and the clone Nem 23 α was deposited at National Institute of Bioscience and Human-Technology Agency of Industrial Science and Technology under the deposit No. of FERM BP-5676. The antibody titer values of the obtained culture broth, ascites and ammonium sulfate precipitation fragments regarding these two clones to *Nitrosomonas europaea* are shown in Table 1. The isotypes of these two clones are shown in Table 2.

TABLE 1

Change of the Specific Activity of an anti-Nitrosomonas europaea Monoclonal Antibody Prepared by Cloning

| | Antibody activity a) | | Protein amount (mg/ml) | | Specific activity b) | |
|---|---|---|---|---|---|---|
| | Nem 7 α | Nem 23 α | Nem 7 α | Nem 23 α | Nem 7 α | Nem 23 α |
| Culture supernatant liquid | 215 | 664 | 8.56 | 5.88 | 25 | 113 |

TABLE 1-continued

Change of the Specific Activity of an anti-Nitrosomonas europaea Monoclonal
Antibody Prepared by Cloning

|  | Antibody activity a) | | Protein amount (mg/ml) | | Specific activity b) | |
| --- | --- | --- | --- | --- | --- | --- |
|  | Nem 7 α | Nem 23 α | Nem 7 α | Nem 23 α | Nem 7 α | Nem 23 α |
| Ascites | 164203 | 217600 | 32.2 | 41.2 | 5099 | 5282 |
| Fragment precipitated by ammonium sulfate | 218700 | 138502 | 15.7 | 16.5 | 13930 | 8394 | a) Antibody activity: ELISA value (Dilution rate of a fused cell-forming antibody at the time of ELISA to an immunogen showing substrate color development of Abs492 = 0.5/Dilution rate of NS-1 at the time of ELISA time immunogen showing substrate color development of Abs492 = 0.5)
b) Specific activity: Antibody activity/Unit protein amount (mg/ml)

TABLE 2

Isotypes of an anti-Nitrosomonas europaea Monoclonal Antibody Prepared by Cloning

|  | Immunoglobulin class | Light chain |
| --- | --- | --- |
| Nem 7 α | IgG2a | δ |
| Nem 23 α | IgG2b | κ |

(2) Test upon the Specificity of Each Monoclonal Antibody

The specificity of the produced two kinds of monoclonal antibodies to *Nitrosomonas europaea* to bacteria present in activated sludge was compared by a color development reaction according to an enzyme antibody assay (ELISA method). Strains employed for the comparison are shown in Table 3 and the results thereof are shown in FIG. 1.

TABLE 3

Strains for Measuring a Cross Reaction Used for an Examination Test of the Antibody Specificity of an anti-Nitrosomonas europaea Monoclonal Antibody prepared by Cloning

| No. | Name of Strain |
| --- | --- |
| 1 | Control |
| 2 | *Flavobacterium sp.* |
| 3 | *Pseudomonas sp.* |
| 4 | *Pseudomonas sp.* |
| 5 | *Enterobacter sp.* |
| 6 | *Aeromonas sp.* |
| 7 | *Corynebacterium sp.* |
| 6 | *Agrobacterium sp.* |
| 9 | *Micromonospora sp.* |
| 10 | *Nocardia amarac* |
| 11 | *Bacillus subtilus* |
| 12 | *Alcaligenes sp.* |
| 13 | *Rhodococcus sp.* |
| 14 | *Alcaligenes denitrificans* |
| 15 | *Bacillus licheniformis* |
| 16 | *Paracoccus denitrificans* |
| 17 | *Pseudomonas stutzeri* |
| 18 | *Pseudomonas fluorescens* |
| 19 | *Pseudomonas picketti* |
| 20 | *Tiobacillus denitrificans* |
| 21 | *Nitrobacter agilis* |
| 22 | *Nitrosomonas europaea* |

As an antigen were used the Pseudomonas genus, the Alcaligenes genus, the Plavobacterium genus and the Actinomyces, which are often reported as preferred species of activated sludge. As is apparent from FIG. 1, the prepared monoclonal antibodies Nem 7 α and Nem 23 α were recognized to have a high specificity to *Nitrosomonas europaea*. These monoclonal antibodies with a high specificity can always have the same specificity, binding capacity and antibody titer, without causing any variability in the result of an inspection, making it possible to standardize properties as a reagent; as described above, it has been revealed that they are useful for detecting nitrifying bacteria present in activated sludge, water or soil convenient, employing reaction characteristics of said antibodies to bacteria such as an agglutination reaction as direct indexes, or employing the color development reaction correlative to said reaction characteristics as an index, or using an antibody-sensitized latex for detection.

(3) Production of a Monoclonal Antibody-Sensitized Latex

A monoclonal antibody produced in the above manner was precipitated with ammonium sulfate and purified with Protein A Column Kit (manufactured by Amersham), and then diluted with a 0.1M glycine-buffered saline solution (pH 8.2) to adjust it to a proper protein concentration. To 1 volume of the monoclonal antibody dilute solution was added 1 volume of a latex H0902 solution with a high specific gravity; the solution were mixed well, and then left to stand at 37° C. for one hour for the antibody to be adsorbed on the latex. Thereafter, a buffer solution containing 1% BSA was added therein to terminate the reaction. After the surplus antibody was removed by washing according to centrifuging, the storage solution was suspended to adjust a latex concentration to 0.25%.

(4) Examination of the Optimum Antibody Protein Concentration at Sensitization

The optimum monoclonal antibody protein concentration at sensitization was examined. Each monoclonal antiboty was examined at antibody protein concentrations for sensitization of 0.01, 0.015, 0.02 and 0.04 (mg/ml).

Regarding other conditions, following conditions were employed; H0902 was employed as a latex with a high specific gravity, sensitization temperature was 37° C., sensitization time was 60 minutes, a glycine-buffered saline solution was employed as a buffer solution, the sensitization latex concentration was 0.25% and agglutination reaction time was from 3 to 15 hours. Regarding the number of bacteria to be compared, since nitrifying bacteria are autotrophic bacteria and the proliferation of the strains are slow, they were measured with a microscope employing a hemocytometer. The results are shown in Table 4.

TABLE 4

Detection of the Optimum Protein Amount of an anti-Nitrosomonas europaea Monoclonal Antibody Used for Coating of Latex Particles

|          | 40 µg/ml | 20 µg/ml            | 15 µg/ml            | 10 µg/ml            |
|----------|----------|---------------------|---------------------|---------------------|
| Nem 7 α  | N.D.     | $5.0 \times 10^5$   | $1.0 \times 10^6$   | $1.0 \times 10^6$   |
| Nem 23 α | N.D.     | $5.0 \times 10^5$   | $1.0 \times 10^6$   | $1.0 \times 10^6$   |

N.D.: Not detected

As shown in Table 4, it has been revealed hat it is possible to analize quantitatively of the number of bacteria in a similar or smaller amount than in the case of employing a polyclonal antibody at a concentration of a protein amount of 0.02 mg/ml.

EXAMPLE 2

Preparation of an anti-*Nitrobacter agilis* Monoclonal Antibody (1) Preparation of Hybridomas and Production of an Ascites Antibody Pure-cultured *Nitrobacter agilis* was washed with a physiological saline solution, and then suspended in a physiological saline solution to adjust the value at an absorbance of 660 nm to 0.5. The obtained suspension (0.2 ml) was injected into a tail vein of a BALB/c mouse, and 10 days after, 0.2 ml of a suspension prepared in the same manner were injected therein to additionally. In addition, the suspension was injected therein to 4 or 5 times in total every 10 days. Before the mouse was slaughtered, 0.2 ml of a suspension prepared in the same manner were injected therein to as the final immunity. On the 4th day after the final immunity, the mouse was killed to extract the spleen thereof, and the spleen cells were suspended in the RPM11640 medium (manufactured by Sigma). A suspension solution of the spleen cell suspension was treated with a 0.82% aqueous ammonium chloride solution at room temperature for 10 minutes, then washed in a serum-free medium twice according to centrifugal separation (250×g), and suspended in a serum-free medium.

Separately, NS-1 cells were proliferated in the RPMI1640 medium containing 15% of fetal bovine serum, then washed in a serum-free medium twice according to centrifugal separation, and subsequently suspended in a serum-free medium. After $4.0 \times 10^7$ spleen cells and $1.0 \times 10^7$ NS-1, cells an a suspended state were mixed, the mixture were subjected to centrifugal separation to precipitate the cells; 1 ml of a serum-free medium containing 45% of polyethylene glycol 6000 was added therein, and the cells were fused at 37° C. for 6 minutes. The obtained cell mixture was washed in a serum-free medium according to centrifugal separation, and then suspended in the RPMI1640 medium containing 15% of fetal bovine serum to adjust to be $1.0 \times 10^5$ spleen cells/ml, and 0.1 ml thereof was introduced into a 96-well plastic microtiter plate, and cultured in an incubator in the presence of 7% hydrocarbon gas.

On the first day after the start of the culture, 0.1 ml of the HAT medium was added therein, and thereafter half of the culture broth was sucked to remove On the second day, on the 4th day, on the 7th day and on the 10th day, and instead of them the HAT medium was added respectively. Colonies of hybridomas, 1 to 2 per well on an average, were grown in 60 to 90% of culture wells of the 96-well plastic microtiter plate. When the hybridomas were proliferated fully (about two weeks after the start of the culture), the antibody titer of the culture supernatant liquid to *Nitrobacter agilis* was examined according to an enzyme immunoassay. Antibodies to *Nitrobacter agilis* were recognized in the culture supernatant liquid of 55 wells of 1536 wells in total. A cloning operation according to limiting dilution was performed twice repeatedly about hybridomas of each well forming antibodies. Thus, clones forming antibodies stably were separated. These clones were named Nam 223 α. The clone Nam 223 α was deposited at National Institute of Bioscience and Human-Technology Agency of Industrial Science and Technology under the name of Hybridoma Nam 223 a , the deposit No. of FERM BP-5677. The isotype of the clone is shown in Table 5.

TABLE 5

Isotype of an anti-Nitrobacter agilis Monoclonal Antibody prepared by Cloning

|           | Immunoglobulin class | Light chain |
|-----------|----------------------|-------------|
| Nem 223 α | IgG2a                | κ           |

(2) Test upon the Specificity of Each Monoclonal Antibody

Figure 2:
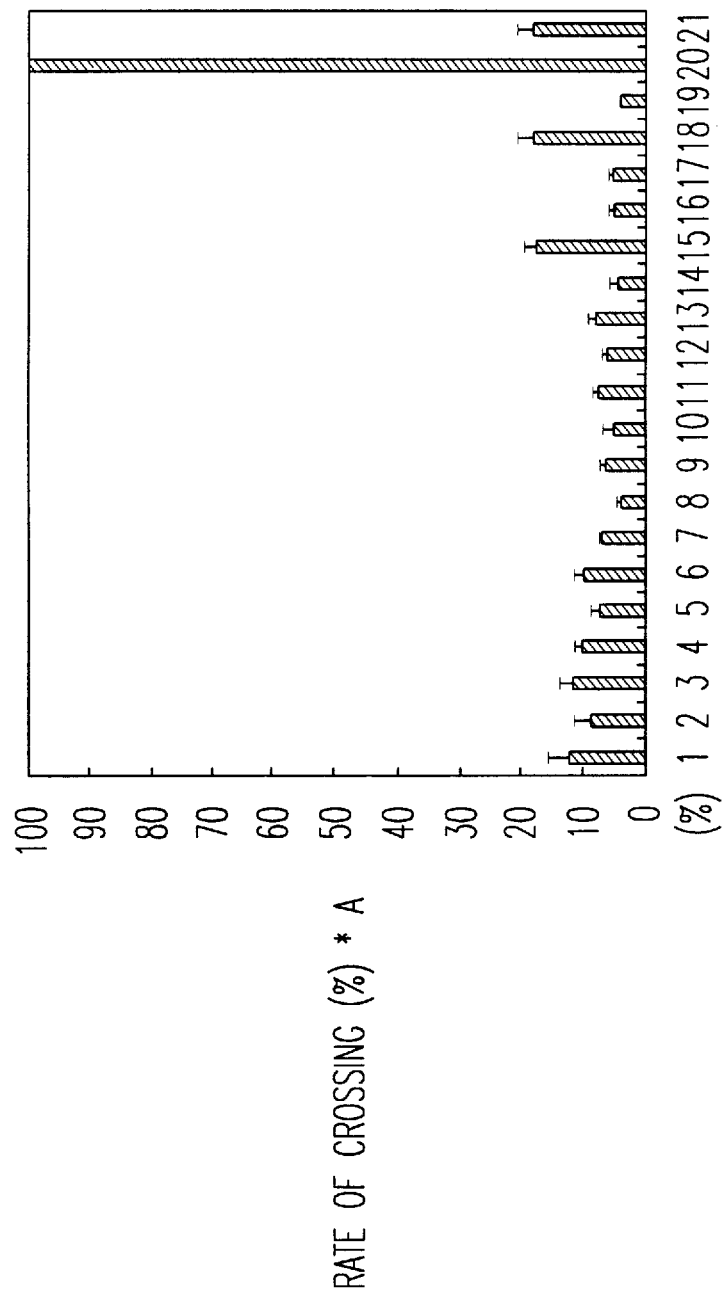
FIG. 2 is an explanatory view regarding the antibody specificity of a monoclonal antibody Nam 223 α.

The antibody specificity of the produced monoclonal antibodies to *Nitrobacter agilis* to bacteria present in activated sludge was compared by a color development reaction according to an enzyme antibody assay (ELISA method). Strains employed for the comparison are shown in Table 6 and the results thereof are shown in FIG. 2.

TABLE 6

Strains or Measuring a Cross Reaction Used for an Examination Test of the Antibody Specificity of an anti-Nitrobacter agilis Monoclonal Antibody prepared by Cloning

| No. | Name of Strain |
|-----|----------------|
| 1   | Control |
| 2   | *Pseudomonas sp.* |
| 3   | *Pseudomonas stutzeri* |
| 4   | *Pseudomonas fluorescens* |
| 5   | *Pseudomonas picketti* |
| 6   | *Pseudomonas aeruginosa* |
| 7   | *Alcaligenes sp.* |
| 8   | *Alcaligenes denitrificans* |
| 9   | *Alcaligenes faecalis* |
| 10  | *Flavobacterium sp.* |
| 11  | *Flavobacterium sp.* |
| 12  | *Paracoccus denitrificans* |
| 13  | *Tiobacillus denitrificans* |
| 14  | *Enterobacter sp.* |
| 15  | *Moraxella sp.* |
| 16  | *Bacillus subtilus* |
| 17  | *Bacillus licheniformis* |
| 18  | *Corynebacterium sp.* |
| 19  | *Nocardia amarae* |
| 20  | *Nitrobacter agilis* |
| 21  | *Nitrosomonas europaea* |

As an antigen were used the Pseudomonas genus, the Alcaligenes genus, the Flavobacterium genus and the Actinomyces. which are often reported as preferred species of activated sludge. As is apparent from FIG. 2, the prepared monoclonal antibody Nam 223 α was recognized to have a high specificity to *Nitrobacter agilis*. These monoclonal antibodies with a high specificity can always have the same specificity, binding capacity and antibody titier, without causing any variability in the result of an inspection, making it possible to standardize properties as a reagent; as described above, it has been revealed that they are useful for detecting nitrifying bacteria present in activated sludge, water or soil convenient, employing reaction characteristics of said antibodies to bacteria such as an agglutination reaction as direct indexes, or employing the color development reaction correlative to said reaction characteristics as an index, or using an antibody-sensitized latex for detection.

(3) Production of a Monoclonal Antibody-Sensitized Latex

A monoclonal antibody produced in the above manner was diluted with a 0.1M glycine-buffered saline solution (pH: 8.2) to adjust it to a proper protein concentration. To 1 volume of the monoclonal antibody dilute solution was added 1 volume of a latex H0902 solution with a high specific gravity; the solution were mixed well, and then left to stand at 37° C. for one hour for the antibody to be adsorbed on the latex. Thereafter, a buffer solution containing 1% BSA was added therein to terminate the reaction. After the surplus antibody was removed by washing according to centrifuging, the storage solution was suspended to adjust a latex concentration to 0.25%.

(4) Examination of the Optimum Antibody Protein Concentration at Sensitization

The optimum monoclonal antibody protein concentration at sensitization was examined. The optimum antibody protein concentration fo each monoclonal antibody was examined changing the concentration of an antibody protein used for sensitization.

Regarding other conditions, following conditions were employed; H0902 was employed as a latex with a high specific gravity, sensitization temperature was 37° C., sensitization time was 60 minutes, a glycine-buffered saline solution was employed as a buffer solution, the sensitization latex concentration was 0.25% and agglutination reaction time was from 3 to 15 hours. Regarding the number of bacteria to be compared, since nitrifying bacteria are autotrophic bacteria and the proliferation of the strains are slow, they were measured with a microscope employing a hemocytometer. The results are shown in Table 7.

TABLE 7

Detection of the Optimum Protein Amount of an anti-Nitrobacter agilis Monoclonal Antibody Used for Coating of Latex Particles

|  | 40 μg/ml | 20 μg/ml | 15 μg/ml | 10 μg/ml |
|---|---|---|---|---|
| Nem 223 α | N.D.* | $4.0 \times 10^5$ | $8.0 \times 10^5$ | $1.6 \times 10^6$ |

N.D: Not detected

As shown in Table 7, it has been revealed that it is possible to analize quantitatively the number of bacteria in a similar or smaller amount than in the case of employing a polyclonal antibody.

Industrial Applicability

As described in detail above, the present invention relates to a monoclonal antibody specific to nitrifying bacteria showing ammonia oxidation activities and nitrite oxidation activities, and serves to make it possible to prepare an antibody always having the same specificity, binding capacity and antibody titer employing monoclonal antibody-forming cells specific to nitrifying bacteria. Moreover, the present invention serves to make it possible to standardize properties of an antibody-sensitized latex reagent employing the above monoclonal antibody, to identify active target microorganisms present in activated sludge, water, soil or microorganism-immobilized carriers more specifically, and to control the number thereof rapidly and properly.

What is claimed is:

1. An anti-*Nitrosomonas europaea* monoclonal antibody recognizing *Nitrosomonas europaea* specifically wherein said monoclonal antibody is selected from the group consisting of monoclonal antibody Nem 7 α produced by hybridoma cell line FERM BP-5675 and monoclonal antibody Nem 23 α produced by hybridoma cell line FERM BP-5676.

2. An antibody-sensitized latex for *Nitrosomonas europaea* comprising a monoclonal antibody specific to *Nitrosomonas europaea* of claim 1 adsorbed on latex particles.

3. An antibody-sensitized latex for *Nitrosomonas europaea*, wherein the latex particles according to claim 2 are latex particles with a high specific gravity of about 1.5 g/cc.

4. An antibody-sensitized latex for *Nitrosomonas europaea* according to claim 3 wherein said latex particles are latex particles with an average particle diameter of about 1.0 μm.

5. A continuous cell line which produces a monoclonal antibody to *Nitrosomonas europaea*, wherein said monoclonal antibody binds to the antigenic determinant recognized by monoclonal antibody Nem 7 μ produced by hybridoma cell line FERM BP-5675, deposited at the National Institute of Bioscience and Human-Technology Agency of Industrial Science and Technology.

6. A continuous cell line which produces a monoclonal antibody to *Nitrosomonas europaea*, wherein said antibody binds to the antigenic determinant recognized by monoclonal antibody Nem 23 α produced by hybridoma cell line FERM BP-5676, deposited at the National Institute of Biosciences and Human-Technology Agency of Industrial Science and Technology.

7. A method for detection and the quantitative analysis of nitrifying bacteria, comprising contacting a sample with a monoclonal antibody-sensitized latex specific for *Nitrosomonas europaea* according to claim 2 or claim 3 and a monoclonal antibody-sensitized latex specific for *Nitrobacter agilis* under conditions that allow binding to occur and detecting the presence and amount of binding between said monoclonal antibody-sensitized latex specific for *Nitrosomonas europaea* and said monoclonal antibody sensitized latex specific for *Nitrobacter agilis* and nitrifying bacteria.

* * * * *